United States Patent [19]

Maeda et al.

[11] 4,018,785
[45] Apr. 19, 1977

[54] CERTAIN 2-IMINOTHIAZOLINE COMPOUNDS

[75] Inventors: Ryozo Maeda, Osaka; Katsumi Hirose, Kishiwada, both of Japan

[73] Assignee: Shionogi & Co., Ltd., Osaka, Japan

[22] Filed: Dec. 3, 1975

[21] Appl. No.: 637,479

[30] Foreign Application Priority Data

Dec. 6, 1974  Japan ................... 49-140766

[52] U.S. Cl. .................. 260/306.7 T; 260/299; 424/200; 424/232; 424/270
[51] Int. Cl.² .............. C07D 277/38; C07D 277/42
[58] Field of Search ................... 260/306.7 T

[56] References Cited
UNITED STATES PATENTS 2,910,478  10/1959  Mizzoni ................... 260/306.7 T

*Primary Examiner*—R. Gallagher
*Attorney, Agent, or Firm*—Wenderoth, Lind & Ponack

[57] ABSTRACT

Thiazoline derivatives represented by the general formula:

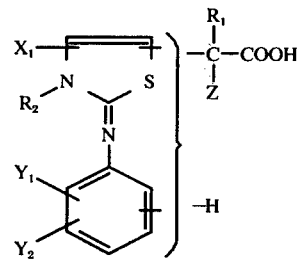

wherein $X_1$ represents hydrogen or methyl; $Y_1$ and $Y_2$ each represents hydrogen, halogen, $C_{1-3}$ alkyl, $C_{1-3}$ alkoxy or trifluoromethyl; $R_1$ represents hydrogen, methyl, or ethyl; $R_2$ represents $C_{1-3}$ alkyl or $C_{3-5}$ alkenyl and Z represents hydrogen, carboxy or carboxy ester group and its esters and pharmaceutically acceptable salts, synthesized by quaternization and acid-elimination reaction being useful as anti-inflammatory, antirheumatic, analgesic and anti-pyretic agents.

21 Claims, No Drawings

CERTAIN 2-IMINOTHIAZOLINE COMPOUNDS

The present invention relates to novel thiazoline derivatives, the intermediates and the pharmaceutically acceptable salts. Further, it relates to the process for their preparation thereof. The said thiazoline derivatives and their pharmaceutically acceptable salts are useful medicament showing anit-inflammatory, analgesic, anti-rheumatic and anti-pyretic activities.

Some thiazole derivatives are known to have anti-inflammatory and analgesic activities (German Open to Public Inspection Application No. P 2450617 published on Apr. 30, 1975). However, the thiazoline derivatives provided by this invention are novel.

The thiazoline derivatives are represented by the general formula:

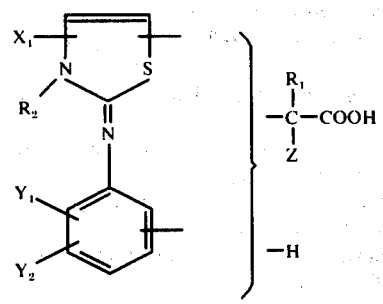

wherein $X_1$ represents hydrogen or methyl, $Y_1$ and $Y_2$ each represents hydrogen, halogen, $C_{1-3}$ alkyl, $C_{1-3}$ alkoxy or trifluoromethyl, $R_1$ represents hydrogen, methyl or ethyl, $R_2$ represents $C_{1-3}$ alkyl or $C_{3-5}$ alkenyl and Z represents hydrogen, carboxy or carboxy ester group.

The following definitions refer to the various terms used throughout this disclosure. The term "$C_{1-3}$ alkyl" refers to the both straight and branched aliphatic radicals having one to three carbon atoms including, for example, methyl, ethyl, propyl, i-propyl. The term "halogen" refers to fluorine, chlorine, and bromine. The term "$C_{1-3}$ alkoxy" includes ether radicals having one to three carbon atoms as exemplified in the term "$C_{1-3}$ alkyl". The term "$C_{3-5}$ alkenyl" includes 2-propenyl, 2-butenyl, 2-methyl-2-propenyl, 3-methyl-2-butenyl. The term "carboxy ester" includes carboxy groups modified with commonly used ester groups such as alkoxy group, aralkyloxy group, aryloxy group, cycloalkyloxy group and the like.

The preferred $Y_1$ and $Y_2$ each is hydrogen and halogen, more preferable is halogen, most preferred are chlorine and fluorine. The preferred $R_1$ is hydrogen or methyl, more preferable is methyl. The preferred $R_2$ is methyl or allyl, especially methyl. As illustrated in the general formula, the group —$CR_1ZCOOH$ may substitute either thiazoline ring or benzene ring. When the group substitutes the benzene ring, preferably 3 or 4 position, more preferably 4 position is substituted.

The compound of the general formula [I] whereof Z is carboxy group or carboxy ester group can be used as intermediate of the objective thiazoline derivatives whereof Z is hydrogen. The esters of the thiazoline derivatives of the formula [I] are also available to obtain the objective compounds and included in the present invention. The ester residue is the same as exemplified in the term "carboxy ester."

Illustrative of the thiazoline derivatives provided by this invention are the following:

2-[3-(3-methyl-4-thiazolin-2-ylideneamino)phenyl]acetic acid,
2-[3-(3,4-dimethyl-4-thiazolin-2-ylideneamino)-phenyl]acetic acid,
2-[4-(3,4-dimethyl-4-thiazolin-2-ylideneamino)-phenyl]acetic acid,
2-[3-chloro-4-(3-methyl-4-thiazolin-2-ylideneamino)-phenyl]acetic acid,
2-[3-fluoro-4-(3-methyl-4-thiazolin-2-ylideneamino)-phenyl]acetic acid,
2-[3,5-dichloro-4-(3,4-dimethyl-4-thiazolin-2-ylideneamino)phenyl]acetic acid,
2-[2-methoxy-4-(3-methyl-4-thiazolin-2-ylideneamino)phenyl]acetic acid,
2-[3-trifluoromethyl-4-(3,5-dimethyl-4-thiazolin-2-ylideneamino)-phenyl]acetic acid,
2-[4-chloro-3-(3-methyl-4-thiazolin-2-ylideneamino)-phenyl]-propionic acid,
2-[4,6-dichloro-3-(3-methyl-4-thiazolin-2-ylideneamino)phenyl]-propionic acid,
2-[6-fluoro-3-(3-methyl-4-thiazolin-2-ylideneamino)-phenyl]-propionic acid,
2-[4-methyl-3-(3-ethyl-5-methyl-4-thiazolin-2-ylideneamino)-phenyl]propionic acid,
2-[4-chloro-3-propyl-4-thiazolin-2-ylideneamino)-phenyl]propionic acid,
2-[4-(3-methyl-4-thiazolin-2-ylideneamino)phenyl]-propionic acid,
2-[4-(3,4-dimethyl-4-thiazolin-2-ylideneamino)-phenyl]propionic acid,
2-[4-(3,5-dimethyl-4-thiazolin-2-ylideneamino)-phenyl]propionic acid,
2-[2-chloro-4-(3,4-diemthyl-4-thiazolin-2-ylideneamino)phenyl]-propionic acid,
2-[2-chloro-4-(3-methyl-4-thiazolin-2-ylideneamino)-phenyl]-propionic acid,
2-[3-chloro-4-(3,4-dimethyl-4-thiazolin-2-ylideneamino)phenyl]-propionic acid,
2-[3-chloro-4-(3-methyl-4-thiazolin-2-ylideneamino)-phenyl]-propionic acid,
2-[2,3-dichloro-4-(3,4-dimethyl-4-thiazolin-2-ylideneamino)-phenyl]propionic acid,
2-[3,5-dichloro-4-(3,4-dimethyl-4-thiazolin-2-ylideneamino)-phenyl]propionic acid,
2-[3,5-dichloro-4-(3-methyl-4-thiazolin-2-ylideneamino)phenyl]-propionic acid,
2-[3,5-difluoro-4-(3-methyl-4-thiazolin-2-ylideneamino)phenyl]-propionic acid,
2-[2-ethoxy-4-(3-methyl-4-thiazolin-2-ylideneamino)-phenyl]-propionic acid,
2-[3-ethyl-4-(3,4-dimethyl-4-thiazolin-2-ylideneamino)phenyl]-propionic acid,
2-[2-fluoro-4-(3,4-dimethyl-4-thiazolin-2-ylideneamino)phenyl]-propionic acid,
2-[2-fluoro-4-(3-methyl-4-thiazolin-2-ylideneamino)-phenyl]-propionic acid,
2-[3-fluoro-4-(3,4-dimethyl-4-thiazolin-2-ylideneamino)phenyl]-propionic acid,
2-[3-fluoro-4-(3-methyl-4-thiazolin-2-ylideneamino)-phenyl]-propionic acid,
2-[3-methoxy-4-(3-methyl-4-thiazolin-2-ylideneamino)phenyl]-propionic acid, 2-[2-methyl-3-chloro-4-(3-methyl-4-thiazolin-2-ylideneamino)-phenyl]propionic acid,
2-[2-methyl-4-(3,4-dimethyl-4-thiazolin-2-ylideneamino)phenyl]-propionic acid,
2-[2-methyl-4-(3-methyl-4-thiazolin-2-ylideneamino)phenyl]-propionic acid,
2-[3-methyl-4-(3,4-dimethyl-4-thiazolin-2-ylideneamino)phenyl]-propionic acid,
2-[3-methyl-4-(3-methyl-4-thiazolin-2-ylideneamino)phenyl]-propionic acid,
2-[3-propoxy-4-(3-methyl-4-thiazolin-2-ylideneamino)phenyl]-propionic acid,
2-[3-propyl-4-(3,5-dimethyl-4-thiazolin-2-ylideneamino)phenyl]-propionic acid,
2-[2-trifluoromethyl-4-(3-methyl-4-thiazolin-2-ylideneamino)phenyl]-propionic acid,
2-[-(3-trifluoromethyl-4-(3-methyl-4-thiazolin-2-ylideneamino)-phenyl]propionic acid,
2-[4-(3-ethyl-4-thiazolin-2-ylideneamino)phenyl]propionic acid,
2-[2-chloro-4-(3-ethyl-4-methyl-4-thiazolin-2-ylideneamino)-phenyl]propionic acid,
2-[3,5-dichloro-4-(3-propyl-4-thiazolin-2-ylideneamino)phenyl]-propionic acid,
2-[2-fluoro-4-(3-propyl-4-methyl-4-thiazolin-2-ylideneamino)-phenyl]propionic acid,
2-{3-chloro-4-[3-(2-propenyl)-4-thiazolin-2-ylideneamino]phenyl}-propionic acid,
2-{5-fluoro-4-[3-(2-methyl-2-propenyl)-4-thiazolin-2-ylideneamino]phenyl}propionic acid,
2-{3-chloro-4-[4-(3-methyl-2-butenyl)-4-thiazolin-2-ylideneamino]phenyl}propionic acid,
2-[3-(3-methyl-4thiazolin-2-ylideneamino)phenyl]-butyric acid,
2-[2-chloro-3-(3,4-dimethyl-4-thiazolin-2-ylideneamino)-phenyl]butyric acid,
2-[6-fluoro-3-(3-methyl-4-thiazolin-2-ylideneamino)-phenyl]-butyric acid,
2-[4-(3,4-dimethyl-4-thiazolin-2-ylideneamino)-phenyl]butyric acid,
2-[3,5-dichloro-4-(3,4-dimethyl-4-thiazolin-2-ylideneamino)-phenyl]butyric acid,
2-[2-fluoro-4-(3-methyl-4-thiazolin-2-ylideneamino)-phenyl]-butyric acid,
2-[2-methoxy-4-(3-methyl-4-thiazolin-2-ylideneamino)phenyl]-butyric acid,
2-[3-trifluoromethyl-4-(3,5-dimethyl-4-thiazolin-2-ylideneamino)phenyl]butyric acid,
2-(2-phenylimino-3,4-dimethyl-4-thiazolin-4-yl)acetic acid,
2-(2-phenylimino-3-methyl-4-thiazolin-4-yl)acetic acid,
2-[2-(3,5-dichlorophenylimino)-3,5-dimethyl-4-thiazolin-4-yl]acetic acid,
2-[2-(4-fluorophenylimino)-3-methyl-4-thiazolin-4-yl]acetic acid,
2-[2-(4-methoxyphenylimino)-3-methyl-4-thiazolin-4-yl]acetic acid,
2-[2-(3-trifluoromethylphenylimino)-3-methyl-4-thiazolin-4-yl]acetic acid,
2-(2-phenylimino-3,4-dimethyl-4-thiazolin-5-yl)acetic acid,
2-[2-(4-chlorophenylimino-3,4-dimethyl-4-thiazolin-4-yl]-acetic acid,
2-[2-(3,5-dichlorophenylimino)-3-methyl-4-thiazolin-5-yl]acetic acid,
2-[2-(4-fluorophenylimino)-3,4-dimethyl-4-thiazolin-5-yl]-acetic acid,
2-[2-(3-methylphenylimino)-3-methyl-4-thiazolin-5-yl]acetic acid,
2-(2-phenylimino-3-methyl-4-thiazolin-4yl)propionic acid,
2-[2-(4-chlorophenylimino)-3,5-dimethyl-4-thiazolin-4yl]-propionic acid,
2-[2-(3,5-dimethylphenylimino)-3-methyl-4-thiazolin-4-yl]-propionic acid,
2-[2-(4-ethylphenylimino)-3,5-dimethyl-4-thiazolin-4-yl]-propionic acid,
2-[2-(2-fluorophenylimino)-3,5-dimethyl-4-thiazolin-4-yl]-propionic acid,
2-[2-(4-methoxyphenylimino)-3,5-dimethyl-4-thiazolin-4-yl]-propionic acid,
2-[2-(4-methylphenylimino)-3-methyl-4-thiazolin-4-yl]propionic acid,
2-[2-(4-propoxyphenylimino)-3,5-dimethyl-4-thiazolin-4-yl]-propionic acid,
2-[2-(3-trifluoromethylphenylimino)-3-methyl-4-thiazolin-4-yl]-propionic acid,
2-(2-phenylimino-3-ethyl-4-thiazolin-4-yl)propionic acid,
2-[2-(4-chlorophenylimino)-3-propyl-4-thiazolin-4-yl]propionic acid,
2-[2-(2-fluorophenylimino)-3-(2-propenyl)-4-thiazolin-4-yl]-propionic acid,
2-[2-phenylimino-3-(2-methyl-2-propenyl)-4-thiazolin-4-yl]-propionic acid,
2-[2-phenylimino-3-(3-methyl-2-butenyl)-4-thiazolin-4-yl]-propionic acid,
2-(2-phenylimino-3,4-dimethyl-4-thiazolin-5-yl)propionic acid,
2-(2-phenylimino-3-methyl-4-thiazolin-5-yl)propionic acid,
2-[2-(4-chlorophenylimino)-3,4-dimethyl-4-thiazolin-5-yl]-propionic acid,
2-[2-(3,5-dichlorophenylimino)-3,4-dimethyl-4-thiazolin-5-yl]-propionic acid,
2-[2-(2-fluorophenylimino)-3,4-dimethyl-4-thiazolin-5-yl]propionic acid,
1-[2-(4-methoxyphenylimino-3,4-dimethyl-4-thiazolin-5-yl]-propionic acid,
2-[2-(2-methylphenylimino-3,4-dimethyl-4-thiazolin-5-yl]-propionic acid,
2-[2-(3-trifluoromethyl)-3-methyl-4-thiazolin-5-yl]propionic acid,
2-(2-phenylimino-3-ethyl-4-methyl-4-thiazolin-5-yl)propionic acid,
2-[2-(3,5-dimethylphenylimino)-3-ethyl-4-thiazolin-5-yl]-propionic acid,
2-(2-phenylimino-3-propyl-4-thiazolin-5-yl)propionic acid,
2-[2-(4-chlorophenylimino)-3-propyl-4-methyl-4-thiazolin-5-yl]-propionic acid,
2-[2-phenylimino-3-(2-propenyl)-4-thiazolin-5-yl]propionic acid,
2-[2-phenylimino-3-(2-methyl-2-propenyl)-4-methyl-4-thiazolin-5-yl]propionic acid,
2-(2-phenylimino-3-methyl-4-thiazolin-4-yl)butyric acid,
2-[2-(4-chlorophenylimino)-3,5-dimethyl-4-thiazolin-4-yl]-butyric acid,
2-[2-(3,5-dichlorophenylimino)-3-methyl-4-thiazolin-4-yl]-butyric acid,
2-[2-(2-fluorophenylimino)-3,5-dimethyl-4-thiazolin-4-yl]-butyric acid,
2-[2-(4-trifluoromethylphenylimino)-3-methyl-4-thiazolin-4-yl]butyric acid, 2-(2-phenylimino-3-methyl-4-thiazolin-5-yl)butyric acid,
2-[2-(3,5-dichlorophenylimino)-3,4-dimethyl-4-thiazolin-5-yl]-butyric acid,
2-[2-(4-fluorophenylimino)-3,4-dimethyl-4-thiazolin-5-yl]-butyric acid and their esters and pharmaceutically acceptable salts.

The thiazoline derivative [I] of this invention can be prepared by many methods, one of which starts with the corresponding thiazole derivative.

The process may be shown as follows in the scheme below:

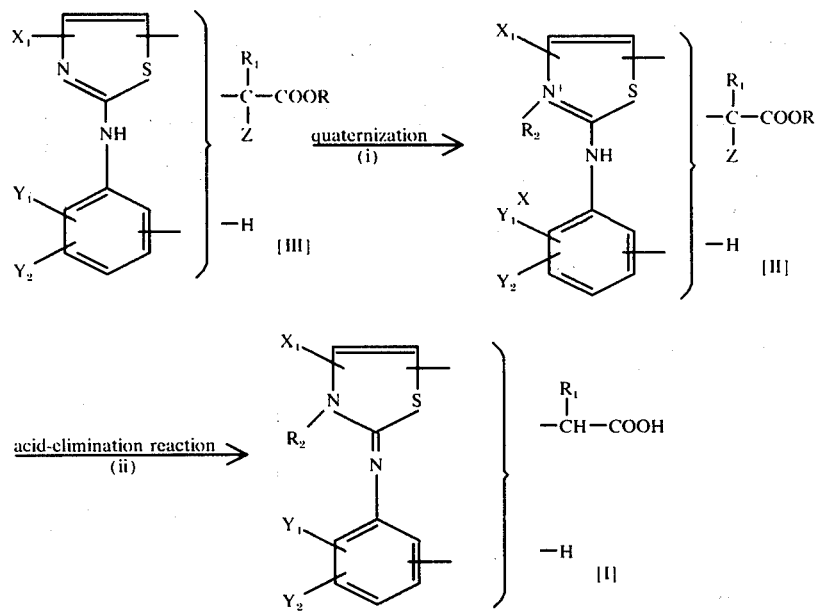

wherein $X_1$, $Y_1$, $Y_2$, $R_1$, $R_2$, and Z each has the same significance designated above, R represent hydrogen or ester residue and $X^-$ represents acid radical.

The starting compound [III] whereof Z is hydrogen is known compound shown in German Open to Public Inspection Application No. P 2450617.0 published on Apr. 30, 1975. The preparation of the starting compound of which Z is carboxy or carboxy ester group is also described in the said patent specification. The compounds may be prepared by modifying α carbon of acetic acid residue with dialkyl carbonate such as diethyl carbonate.

As shown in the above scheme, the starting compound [III] is subjected to quaternization. The quaternization may be effected with quaternizing agent, for example, alkyl halogenide (e.g. iodide, bromide or chloride of alkyls such as methyl, ethyl, propyl or isopropyl), alkenyl halogenide (e.g. iodide, bromide or chloride of alkenyl such as 2-propenyl, 2-butenyl, 2-methyl-2-propenyl, 3-methyl-2-butenyl), aromatic sulfonic acid alkyl ester (e.g. benzenesulfonic acid alkyl ester, p-toluenesulfonic acid alkyl ester), or diaklyl sulfate (e.g. dimethyl sulfate, diethyl sulfate). While reaction solvent is not necessarily required, inactive neutral solvent may be used, e.g. an alcohol (e.g. methanol or ethanol), a hydrocarbon (e.g. benzene, toluene or xylene), an ether, (e.g. ether or tetrahydrofuran), dimethylformamide or a mixture thereof. The reaction can be effected at a temperature of from room temperature to 150° C for 1 to 180 hours, though the reaction temperature and reaction time may be properly changed in accordance with other reaction conditions. The reaction can be acceralated by applying pressure.

The resultant quaternary ammonium salt [II] is subjected to acid-elementation reaction symbolized (ii) in the above scheme. Hydrohalogenic acid or aromatic sulfonic acid may be eliminated from compound [II]. The reaction is effected with acid-eliminating agent, e.g. an alkali metal hydroxide (e.g. sodium hydroxide or potassium hydroxide), an alkali metal carbonate (e.g. sodium carbonate or potassium carbonate), an alkali metal hydrogencarbonate (e.g. sodium hydrogencarbonate or potassium hydrogencarbonate) or ammonia. The reaction is preferably effected in solvent, e.g. water, a halogenohydrocarbon (e.g. chloroform or methylene chloride), a hydrocarbon (e.g. benzene, toluene or xylene) or an ether (e.g. ether, dioxane, tetrahydrofuran, 1,2-dimethoxyethane, ethyleneglycol dialkyl ether or diglyme). The reaction may be effected by stirring the compound [II] with the above acid-eliminating agent in the presence or not of solvent.

The resultant product may be hydrolyzed if necessary. The hydrolysis may be effected in a usual manner used to carboxylic acid esters. The product is hydrolyzed with an acid (e.g. hydrochloric acid, sulfuric acid, hydrobromic acid or acetic acid) or a base (e.g. sodium hydroxide, potassium hydroxide, sodium carbonate, potassium carbonate, sodium hydrogencarbonate or potassium hydrogencarbonate) in water or suitable organic solvent containing water.

The compound [II] of which Z is carboxy or carboxy ester group is further subjected to decarboxylation, though decarboxylation is occasionally completed during acid-elimination reaction or hydrolysis. The decarboxylation is easily effected by a usual method such as heating the compound [II].

Besides, the above hydrolysis and decarboxylation are sumultaneously accomplished when the acid-elimination reaction is effected under severe conditions such as treatment with sodium hydroxide or potassium hydroxide.

Thus obtained compound [I] can be converted to the pharmaceutically acceptable non-toxic salts in conventional manner in accordance with requirement for separation, purification, formulation and the like. Such salts include, for example, alkali metal salts (e.g. sodium salt, potassium salt, lithium salt), alkaline earth metal salts (e.g. calcium salt, magnesium salt, barium salt) and aluminum salt.

Further, the compounds of this invention may form pharmaceutically acceptable non-toxic salts with a variety of inorganic or organic acids. There are exemplified the hydrochloride, hydrobromide, hydroiodide, sulfate, nitrate, phosphate, thiocianate, carbonate, acetate, oxalate, succinate, maleate, tartarate, citrate, benzoate, salicylate and phtbalate salts.

Besides, the thiazoline derivative [I] is an optically active compound and may be resolved into d- and l-isomers. The optical resolution can be effected in a conventional manner and both isomers can be used solely or as a mixture depending on the therapeutical requirement.

The compounds of this invention including the pharmaceutically non-toxic salts exhibit anti-inflammatory, anti-rheumatic, analgesic and anti-pyretic activities.

The pharmacological activity was examined by the following methods. The results are shown in Table 1.

Test Method

1. Acetic Acid Writhing Method

DS mice (20-23 g, male) are treated with an intraperitoneal injection of 0.1 ml/10 g of 0.6 % acetic acid 60 minutes after oral administration of a test compound. The number of times of writhing for 10 minutes is counted. The $ED_{50}$ is calculated by the Bliss' method.

2. Effect on Yeast-inflamed Foot

A test compound is orally given Wistar rat (180–200 g, female) immediately before subcutaneous injection of 0.1 ml of 20 % yeast suspension into the plantar tissue of the foot. Two hours later, the pain threshold is measured by compressing the foot with a plunger and calculated by the method of Litchfield and Wilcoxon [J. Pharmacol. Exp. Ther. 96, 99-113 (1949)].

3. Effect on Adjuvant Arthritis

Wistar rat (140-160 g, female) exhibiting a typical arthritis in the foot by the 21st day after intradermal injection of dead tubercle bacilli is selected for the test. A test compound is orally administered to the arthritic rat twice a day for 5 consecutive days. Five hours after the final medication the change in swelling volume of the arthritic foot is measured. The $ED_{30}$ is calculated by the Bliss' method.

4. Anti-edema Activity

An aqueous solution of 1 % carrageenin (0.05 ml) is used as phlogistic agent. After 30 minutes Wistar rats (180–200 g, female) are orally administered test compounds, the phlogistic agent is injected subcutaneously into the plantar part of the foot of rats. The volume of swelling is measured 3 hours after carrageenin, and the anti-edema activity is determined by calculating the ratio of the edematous volume of medicated foot to that of non-medicated foot. The $ED_{50}$ is calculated by the Bliss' method.

5. Anti-pyretic Activity

A test compound is orally administered to Wistar rat (180–200 g, female) 16 hours after an injection of 2 ml of 15 % suspension of yeast into the subcutaneous tissue of the hip of the rat. The rectal temperature is measured every 1 hour for 5 hours. The effective dose is calculated by the Bliss' method.

6. Acute Toxity

Ten DS mice (20–23 g, male) or ten Wistar rate (180–200 g, female) a group are used at one dose level. The $LD_{50}$ after 72 hours of oral administered of a test compound is determined. The $LD_{50}$ is calculated by the Bliss' method.

Table 1

| Result Assay Item | Drug mg/kg ED(%) | Indomethacin | Me fenamic Acid | Phenylbutazone | Comp. 1 | Comp. 2 | Comp. 3 | Comp. 4 |
|---|---|---|---|---|---|---|---|---|
| 1. Acetic Acid Writhing | 50 | 6.5 | 203 | 430 | 6.8 | 11 | 18 | 21 |
| 2. Yeast-inflamed Food | 100 | 23 | 110 | 120 | 14 | 5.4 | 7.2 | 7.8 |
| 3. Arthritis | 30 | 1 | 37 | 9 | 23 | 9 | 41 | 25 |
| 4. Anti-edema | 30 | 4.5 | 15 | 48 | 4.1 | 0.25 | 1.6 | 3.2 |
| 5. Anti-pyretic | −0.5° C | 0.9 | 1.2 | 4 | 3 | 1.3 | 0.6 | 1.6 |
| 6. Acute Toxity Mouse | Mouse | 17 | 2103 | 1414 | 750(p) | 750(p) | 1250(p) | 750(p) |
| | Rat | 51 | 2750 | 874 | 750(p) | 500(p) | >1000(p) | 750(p) |

Note:
Comp. 1 : 2-[3-Chloro-4-(3-methyl-4-thiazolin-2-ylidenamino)phenyl]propionic acid
Comp. 2 : 2-[3-fluoro-4-(3-methyl-4-thiazolin-2-ylideneamino)phenyl]propionic acid
Comp. 3 : 2-[3,5-dichloro-4-(3-methyl-4-thiazolin-2-ylideneamino)phenyl]propionic acid
Comp. 4 : 2-[3,5-dichloro-4-(3,4-dimethyl-4-thiazolin-2-ylideneamino)phenyl]propionic acid
P : presumption As shown in Table 1, the thiazoline derivatives of this invention exhibit anti-inflammatory, analgesic, anti-rheumatic and anti-pyretic activities stronger than the commercially available compounds, i.e. indomethacin, mefenamic acid and phenylbutazone. The $ED_{30}$ value of anti-edema activity of calcium 2-[2-fluoro-4-(3,4-dimethyl-4-thiazolin-2-ylideneamino)phenyl]propionate and calcium 2-(3-methyl-2-phenylimino-4-thiazolin-4-yl)propionate is 7.1 mg/kg and 16.4 mg/kg respectively. The other compounds of this invention have the same pharmacological activities.

Thus, the compounds [I] and the pharmaceutically acceptable salts are useful in treatment of various inflammations, pains and rheumatic diseases of human being and animals.

The compounds of this invention can be administered solely or in combination with a pharmaceutically acceptable carrier orally, percutaneously or by injection. Preferably, the compounds are employed in combination with one or more carriers suited to the particular route of administration. The carrier to be used is determined by the solubility and chemical property of the compound and the route of administration. There are exemplified as solid carrier for internal or external use, lactose, sucrose, starch, dextrin, sodium hydrogencarbonate, licorice powder, talc, kaoline, bentonite, calcium carbonate, paraffin and as gel or liquid carrier, gelatine, water, ethanol, i-propanol, chloroform, glycerol, and the like. Freon (Trade Mark) is also available for aerosols.

Practical examples of suitable pharmaceutical preparations of compound [I] are tablet, capsules, pills, ointment, granules, powders, suppositories, aerosols or injectable solutions.

Therapeutic composition comprises 1 mg – 500 mg of one or more compound of general formula [I] with or without a pharmaceutically acceptable carrier. The compound [I] is generally administered to human being and animals in the order of the same to one thirtieth of the practical dosage of mefenamic acid, i.e. 20 – 1000 mg of compound [I] can be administered to man orally either in singlet or divided doses over a period of 24 hours. The compound is also administered at once for acute diseases.

The following examples are given solely for the purpose of illustration and not to be construed as limitation of the present invention.

EXAMPLE 1

2-[4-(3-Methyl-4-thiazolin-2-ylideneamino)phenyl]-propionic acid

1. A mixture of ethyl 2-[4-(N-thiazol-2-ylamino)-phenyl]propionate (6.3g), methyl iodide (30 ml) and ethanol (30 ml) is heated at 50°–55° C for 20 hours under nitrogen atmosphere. After evaporation of ethanol and methyl iodide, the resultant residue is washed with ether and ethyl acetate successively to give 3-methyl-2-[4-(1-ethoxycarbonylethyl)anilino]-thiazolium iodide (8.0 g). (Yield 84 %).

2. The product is dissolved in methylene chloride. The solution is washed with 10% aqueous potassium carbonate solution and evaporated to remove methylene chloride. The resultant residue is dissolved in ether. The solution is dried over potassium carbonate and evaporated to remove ether. The residue is ethyl 2-[4-(3-methyl-4-thiazolin-2-ylideneamino)phenyl]-propionate (5.5 g). (Yield 83%).

IR $\nu_{max}^{CCl_4}$ cm$^{-1}$ 1735, 1615, 1590.

NMR $\tau_{CDCl_3}$ 2.9 (4H, Aromatic), 3.5 (d, 1H), 4.2 (d 1H), 5.9 (q, 2H), 6.3 (q, 2H), 6.6 (s, 3H), 8.5 (d, 1H), 8.8 (t, 3H).

(3) The product (5.5 g) is dissolved in a mixture of 20% aqueous potassium hydroxide solution (28 ml) and ethanol (28 ml) and the solution is kept at room temperature for 1 hour. After evaporation of ethanol, the solution is neutralized with hydrochloric acid, adjusted to pH 5 with acetic acid, subjected to salting-out with sodium chloride and then extracted with ether. The ether solution is dried over magnesium sulfate and evaporated. The residue is recrystallized from ethyl acetate to give 2-[4-(3-methyl-4-thiazolin-2-ylideneamino)phenyl]-propionic acid (4.3 g) melting at 130°–132° C. (Yield 73%).

IR $\nu_{max}^{Nujol}$ cm$^{-1}$ 1710, 1595.

Anal. Calcd. for $C_{13}H_{14}O_2N_2S$: C, 59.52; H, 5.36; N, 10.64; S, 12.18. Found: C, 59.79; H, 5.36; N, 10.41; S, 12.18.

The corresponding hydrochloride recrystallized from ethanol melts at 154°–155° C.

IR $\nu_{max}^{Nujol}$ cm$^{-1}$ 1708, 2470 (broad).

EXAMPLE 2

2-[3,5-Dichloro-4-(3-methyl-4-thiazolin-2-ylideneamino)phenyl]propionic acid

1. A solution of ethyl 2-[3,5-dichloro-4-(N-thiazol-2-ylamino)phenyl]propionate (14 g) in methyl iodide (70 ml) is refluxed on an oil bath of 50°–55° C with stirring. After removal of methyl iodide, the resultant residue is dissolved in methylene chloride. The solution is washed with 20% aqueous potassium carbonate solution three times, drived over potassium carbonate and evaporated to remove methylene chloride. The resultant oily residue is subjected to column chromatography using silica gel. From benzene and 2% ether/benzene eluents ethyl 2-[3,5-dichloro-4-(3-methyl-4-thiazolin-2-ylideneamino)phenyl]propionate (7.2 g) is obtained.

IR $\nu_{max}^{CCl_4}$ cm$^{-1}$ 1738, 1735, 1620.

2. A solution of the above product (6.0 g) in a mixture of ethanol (30 ml) and 20% aqueous potassium hydroxide solution (30 ml) is kept at room temperature for 1 hour. After evaporation of ethanol the resultant solution is neutralized with hydrochloric acid and adjusted to pH 5 with acetic acid to give 2-[3,5-dichloro-4-(3-methyl)-4-thiazolin-2-ylideneamino)phenyl]propionic acid as precipitate. The precipitate is filtered off, washed with water and dried to give crystals (5 g) melting at 161°–165° C. Recrystallization from ethyl acetate gives crystals melting at 165°–167° C. (Yield 84%).

IR$\nu_{max}^{Nujol}$ cm$^{-1}$ 3125, 3075, 1710, 1600.

Anal. Calcd. for $C_{13}H_{12}O_2N_2SCl_2$ C, 47.13; H, 3.65; N, 8.46; S, 9.68; Cl, 21.40. Found: C, 47.37; H, 3.69; N, 8.67; S. 9.56; Cl, 21.17.

The product (2.4 g) is dissolved in an aqueous solution (33 ml) of sodium hydroxide (0.3 g). The solution is washed with ether and an aqueous solution (2 ml) of calcium chloride dihydrate (533 mg) is added to the solution. The precipitated crystals are filtered off to give the objective calcium salt (2.5 g) melting at 265°–270° C (decomp.).

EXAMPLE 3

2-[3-Chloro-4-(3-methyl-4-thiazolin-2-ylideneamino)-phenyl]propionic acid

1. A mixture of ethyl 2-[3-chloro-4-(N-thiazol-2-ylamino)phenyl]propionate (3.8 g), methyl iodide (11.4 ml) and ethanol (11.4 ml) is heated at 100° C for 6 hours in a sealed tube. The ethanol and methyl iodide are evaporated. The residue is washed with benzene and dissolved in methylene chloride. The solution is washed with 20% aqueous potassium carbonate solution and evaporated to remove methylene chloride. The residue is treated in the same manner as in Example 1 to give ethyl 2-[3-chloro-4-(3-methyl-4-thiazolin-2-ylideneamino)phenyl]propionate (2.45 g). (Yield 62%).

IR $\nu_{max}^{CCl_4}$ cm$^{-1}$ 1735, 1615, 1585.

2. The product is hydrolyzed in the same manner as in Example 1 (3) and recrystallized from ether/hexane to give 2-[3-chloro-4-(3-methyl-4thiazolin-2-ylideneamino)phenyl]propionic acid (2.08 g) melting at 132°–133° C.

IR $\nu_{max}^{Nujol}$ cm$^{-1}$ 2500 (broad), 1950 (broad), 1720, 1580.

Anal. Calcd. for $C_{13}H_{13}O_2N_2SCl$: C, 52.61; H, 4.42; N, 9,44; s, 10.80; Cl, 11.95. Found: C, 52.83; H, 4.61; N, 9.40; S, 10.90; Cl, 11.84.

EXAMPLE 4

2-[2-Chloro-4-(3,4-dimethyl-4-thiazolin-2-ylideneamino)phenyl]propionic acid

1. A solution of ethyl 2-{2-chloro-4-[N-methylthiazol-2-yl)amino]phenyl}propionate (9.0 g) in methyl iodide (50 ml) is refluxed on an oil bath of 50° C for 20 hours with stirring to give a precipitate. The methyl iodide is evaporated. The residue is washed with ethyl acetate and recrystallized from ethanol/ethyl acetate and aqueous ether successively to give 3,4-dimethyl-2-[2-chloro-4-(1-ethoxycarbonylethyl)anilino]-thiazolium iodide (7.7 g) melting at 199°–202° C. (Yield 60 %).

IR $\nu_{max}^{Nujol}$ cm$^{-1}$ 3075, 1730, 1608.

Anal Calcd. for $C_{16}H_{20}O_2N_2SCII$: C, 41.17; H, 4.32; N, 6.00; S, 6.87; Cl, 7.60; I, 27.19. Found: C, 40.96; H, 4.32 N, 6.01; S, 6.79; Cl, 7.61; I, 27.17.

2. The product (7.7 g) is dissolved in methylene chloride. The solution is washed with 20% aqueous solution of potassium carbonate three times, dried over potassium carbonate and evaporated. The residue is subjected to column chromatography using alumina. From benzene eluant ethyl 2-[2-chloro-4-(3,4-dimethyl-4-thiazolin-2-ylideneamino)phenyl]propionate (5.6 g) is obtained as oily residue.

IR $\nu_{max}^{CCl_4}$ cm$^{-1}$ 1733, 1615.

3. To the product (5.6 g) is added ethanol (30 ml) and 20% aqueous potassium hydroxide solution (30 ml). The solution is kept at room temperature for 1 hour and evaporated. The residue is neutralized and adjusted to pH 5 with hydrochloric acid and extracted with ether. The extract is washed with water, dried over magnesium sulfate and evaporated. The resultant residue (5.0 g) is crystallized from acetone/hexane to give crystals (4.4 g) melting at 132°–133° C. (Yield 86%).

IR $\nu_{max}^{Nujol}$ cm$^{-1}$ 2450, 1900, (broad), 1718, 1608.

Anal. Calcd. for $C_{14}H_{15}O_2N_2SCl$: C, 54.10; H, 4.86; N, 9.01; S, 10.32; Cl, 11.41. Found: C, 54.38; H, 4.84; N, 8.95; S, 10.38; Cl, 11.40.

EXAMPLE 5

2-[3-Fluoro-4-(3-methyl-4-thiazolin-2-ylideneamino)-phenyl]propionic acid

1. A mixture of ethyl 2-[3-fluoro-4-(N-thiazol-2-ylamino)phenyl]propionate (11.1 g), methyl iodide (44.5 ml) and ethanol (44.5 ml) is heated at 50°–55° C for 48 hours. The resultant mixture is treated in the same manner as in Example (1) and (2) to give ethyl 2-[3-fluoro-4-(3-methyl-4-thiazolin-2-ylideneamino)-phenyl]propionate (6.8 g). (Yield 58.5%).

IR $\nu_{max}^{CCl_4}$ cm$^{-1}$ 1730, 1620, 1600.

2. The product (6.8 g) is hydrolyzed in the same manner as in Example 1 (3) gives 2-[3-fluoro-4-(3-methyl-4-thiazolin-2-ylideneamino)phenyl]propionic acid (5.9 g). Recrystallization from ethyl acetate and 10% acetone/ethyl acetate successively gives crystals melting at 151°–152° C. (Yield 75 %).

IR $\nu_{max}^{Nujol}$ cm$^{-1}$ 2500 (broad), 1900 (broad), 1710, 1580.

Anal. Calcd. for $C_{13}H_{13}O_2N_2SF$: C, 55.70; H, 4.64; N, 9.99; S, 11.44; F, 6.78. Found: C, 55.60; H, 4.93; N, 9.93; S, 11.57; F, 6.84.

EXAMPLE 6

2-[2-Chloro-4-(3-methyl-4-thiazolin-2-ylideneamino)-phenyl]propionic acid

1. A mixture of 2-[3-chloro-4-(1-diethoxycarbonylethyl)anilino]thiazole (6.5 g), methyl iodide (40 ml) and ethanol (40 ml) is heated at 50° C for 24 hours. The similar procedure as in Example 1 (1) gives 3-methyl-2-[3-chloro-4-(1-diethoxycarbonylethyl)anilino]thiazolium iodide (5.2 g). Recrystallization from ethanol gives crystals melting at 192°–193° C.

IR $\nu_{max}^{Nujol}$ cm$^{-1}$ 1743, 1720.

Anal. Calcd. for $C_{18}H_{22}O_4N_2SCII$: C, 41.19; H, 4.23; N, 5.34; S, 6.11; Cl, 6.76; I, 24.18. Found: C, 41.20; H, 4.15; N, 5.29; S, 5.99; Cl, 6.56; I, 24.11.

2. A suspension of the product (8.8 g) in methylene chloride is washed with 20% aqueous potassium carbonate solution. The solution is washed with water, dried over potassium carbonate and evaporated to remove methylene chloride. The residue is subjected to alumina column chromatography eluted with benzene. Evaporation of solvent gives diethyl 2-methyl-2-[2-chloro-4-(3-methyl-4-thiazolin-2-ylideneamino)-phenyl]malonate (6.3 g). (Yield 94.5%).

3. The product (6.3 g) is dissolved in a mixture of ethanol (33 ml). and 20% aqueous potassium hydroxide solution (33ml). The solution is kept at room temperature for 16 hours. The ethanol is evaporated. The resultant solution is adjusted to pH 6 with hydrochloric acid, and evaporated to dryness under reduced pressure. The residue is extracted with hot acetone. Evaporation of acetone gives a residue, 2-methyl-2-[2-chloro-4-(3-methyl-4-thiazolin-2-ylideneamino)-phenyl]malonic acid which decomposes at 90° C. The residue is heated on a water bath for 10 minutes. A dilute aqueous solution of sodium hydrogencarbonate is added to the residue. The solution is washed with chloroform and ether respectively, treated with active carbon, adjusted to pH 6 with hydrochloric acid and evaporated to dryness. The resultant residue is extracted with hot acetone and evaporated. The residue is recrystallized from 10% ethanol/acetone to give 2-[1-chloro-4-(3-methyl-4-thiazolin-2-ylideneamino)phenyl]propionic acid (3.4 g) melting at 215°–220° C (decomp.).

IR $\nu_{max}^{Nujol}$ cm$^{-1}$ 2775, 2450, 2000–1900 (broad), 1730, 1715, 1610.

Anal. Calcd. for $C_{13}H_{13}O_2N_2SCl$: C, 52.61; H, 4.42; N, 9.44; S, 10.80; Cl, 11.95. Found: C, 52.83; H, 4.48; N, 9.28; S, 10.84; Cl, 12.08.

EXAMPLE 7

2-[3-Chloro-4-(3-methyl-4-thiazolin-2-ylideneamino)-phenyl]acetic acid

1. A mixture of ethyl 2-[3-chloro-4-(N-thiazol-2-ylamino)phenyl]acetate (8.9 g), methyl iodide (44 ml) and ethanol (44 ml) is heated at 50°–55° C for 42 hours with stirring. The ethanol and methyl iodide are evaporated and the residue is washed with ether and kept at room temperature to give a precipitate. The precipitate is washed with ethyl acetate and cold acetone successively and recrystallized from acetone to give 3-methyl-2-[2-chloro-4-(ethoxycarbonylmethyl)anilino]-thiazolium iodide (6.6 g) melting at 147°–148° C.

2. The solution of the product (6.6 g) in methylene chloride is washed with 10% aqueous potassium carbonate/solution three times and dried over potassium carbonate. The evaporation of the solvent gives ethyl 2-[3-chloro-4-(3-methyl-4-thiazolin-2-ylideneamino)-phenyl]acetate (4.62 g). (Yield 100%).

IR $\nu_{max}^{CCl_4}$ cm$^{-1}$ 1740, CCl

3. The above product (4.62 g) is hydrolyzed in the same manner as in Example 1 (3) to give crystals melting at 155°–158° C. Recrystallization from ethyl acetate and acetone successively gives pure objective compound (3.48 g) melting at 158°–159° C. (Yield 83.5%).

IR $\nu_{max}^{Nujol}$ cm$^{-1}$ 2500 (broad), 1700, 1570.

Anal. Calcd. for $C_{12}H_{11}O_2N_2SCl$: C, 50.98; H, 3.92; N, 9.91; S, 11.34; Cl, 12.54. Found: C, 50.98 H, 3.97; N, 9.71; S, 11.31; Cl, 12.66.

EXAMPLE 8

2-[3-Chloro-4-(3-allyl-4-thiazolin-2-ylideneamino)-phenyl]propionic acid

1. A mixture of ethyl 2-[3-chloro-4-(N-thiazol-2-ylamino)phenyl]propionate (12 g), allyl bromide (6.1 g) and ethanol (25 ml) is heated at 70°–75° C for 8 days. The ethanol is evaporated and the residue is washed with ether, then dissolved in methylene chloride. The solution is washed with an aqueous potassium carbonate solution and dried over potassium carbonate. The methylene chloride is evaporated to give oily residue (12.3 g). The residue is acetylated with anhydrous acetic acid (48 ml) under heating at 120°–125° C for 3 hours. The resultant mixture is dissolved in benzene and extracted with 10% hydrochloric acid. The extract is washed with benzene, made alkaline with sodium hydrogen carbonate and then extracted with ether. The residue obtained after evaporation of the ether is subjected to column chromatography using silica gel. From 50% hexane/benzene eluent and hexane/benzene (1:2), ethyl 2-[3-chloro-4-(3-allyl-4-thiazolin-2-ylideneamino)phenyl]-propionate (3.3 g) is obtained. (Yield 24.5%).

IR $\nu_{max}^{CCl_4}$ cm$^{-1}$ 1735, 1610, 1590.

2. The above product (3.3 g) is hydrolyzed in the same manner as in Example 1 (3) to give the objective compound (3.0 g). Recrystallization from ether/hexane gives pure product (2.78 g) melting at 114°–115° C. (Yield 92.5%).

IR $\nu_{max}^{Nujol}$ cm$^{-1}$ 2500 (broad), 1950 (broad), 1720, 1600, 1570, 1550.

Anal. Calcd. for $C_{15}H_{15}O_2N_2SCl$: C, 55.81; H, 4.68; N, 8.68; S, 9.93; Cl, 10.98. Found: C, 55.94; H, 4.69; N, 8.72; S, 9.90; Cl, 11.02.

EXAMPLE 9

Calcium 2-(2-phenylimino-3-methyl-4-thiazolin-4-yl)propionate

1. A mixture of ethyl 2-(2-anilinothiazol-4-yl)-propionate (6.15 g), methyl iodide (17 ml) and ethanol (17 ml) is heated at 100° C for 11.5 hours in a sealed tube. The resultant mixture is treated with potassium carbonate in the same manner as in Example 1 (2) to give ethyl 2-(2-phenylimino-3-methyl-4-thiazolin-4-yl)propionate (1.6 g) melting at 80°–81° C (recrystallized from ether/hexane).

IR $\nu_{max}^{CCl_4}$ cm$^{-1}$ 1740, 1610, 1580, 690.

Anal. Calcd. for $C_{15}H_{18}O_2NS$: C, 62.04; H, 6.25; N, 9.65; S, 11.04. Found: C, 62.20; H, 6.24; N, 9.70; S, 11.03.

2. The product (1.6 g) is dissolved in a mixture of 95% ethanol (8 ml) and 20% aqueous solution of potassium hydroxide (8 ml). The solution is kept at room temperature for 1 hour. After evaporation of ethanol, the residue is dissolved in water. The solution is neutralized with hydrochloric acid and washed with ether. The addition of calcium chloride dihydrate (405 mg) results in a precipitate. The precipitate is filtered off and washed with water to give calcium 2-(2-phenylimino-3-methyl-4-thiazolin-4-yl)propionate (1.56 g) melting at 152-153 (decomp.).

IR $\nu_{max}^{Nujol}$ cm$^{-1}$ 3300 (broad), 1550 (broad).

Anal. Calcd. for $(C_{13}H_{13}O_2N_2S)_2Ca.3H_2O$: C, 50.63; H, 5.23; N, 9.08; Ca, 6.50. Found: C, 50.62; H, 5.21; N, 8.95; Ca, 6.54. (Note: Carbon dioxide was released from carboxy group during elemental analysis.)

EXAMPLE 10

Calcium 2-[2-(4-chlorophenylimino-3,4-dimethyl-4-thiazolin-5-yl]acetate

1. A mixture of ethyl 2-[2-(4-chlorophenylamino)-4-methyl-thizaol-5-yl)acetate (7.0 g) and methyl iodide (35 ml) is refluxed on an oil bath of 40° C for 24 hours with stirring. The methyl iodide is evaporated and the residue is dissolved in ether/ethyl acetate to give a precipitate. The precipitate is filtered off and crystallized from ethanol/ethyl acetate to give 2-(4-chlorophenylamino)-3,4-dimethyl-5-ethoxycarbonyl-methylthiozolium iodide melting at 163°–164° C. (Yield 72.5%).

Anal. Calcd. for $C_{15}H_{18}O_2N_2SClI$: C, 39.79; H, 4.01; N, 6.18; S, 7.08; Cl, 7.83; I, 28.03. Found: C, 39.86; H, 4.00; N, 6.21; S, 6.80; Cl, 7.58; I, 27.89.

2. The product (7.4 g) is suspended in methylenechloride (50 ml). The suspension is treated with 20% aqueous potassium carbonate solution three times and dried over potassium carbonate to give a residue. The residue is subjected to column chromatography using alumina eluted with benzene. From eluent ethyl 2-[2-(4-chlorophenylimino)-3,4-dimethyl-4-thiazolin-5-yl)acetate](5.2 g). (Yield 98%).

IR $\nu_{max}^{CCl_4}$ cm$^{-1}$ 1738, 1640, 1600.

3. To the above product (3.0 g) is added 20% aqueous potassium hydroxide solution (15 ml) and ethanol (15 ml). The solution is kept at room temperature for 1 hour. After evaporation of ethanol, the solution is adjusted to pH 7 with hydrochloric acid and calcium chloride dihydrate (0.68 g) is added to the solution. The solvent is evaporated and the residue is extracted with hot ethanol/acetone. After insoluble substances are filtered off, the extract is evaporated to remove ethanol and acetone. The residue is recrystallized from hexane to give crystals melting at 186°–192° C. The crystals are washed with ether and recrystallized from ether to give crystals melting at 198°–201° C (1.20 g). (Yield 38.5%).

Anal. Calcd. for $(C_{13}H_{12}O_2N_2SCl)_2Ca.2.5H_2O$: C, 46.14; H, 4.32; N, 8.28; Cl, 10.48; Ca. 5.92. Found: C, 46.42; H, 4.42; N, 8.28; Cl, 10.51; Ca, 5.53.

EXAMPLES 11–25

The following compounds are prepared by the similar procedures as in Examples 1–8.

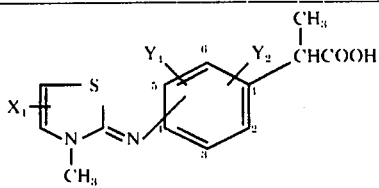

| Ex. No. | $X_1$ | $Y_1$ | $Y_2$ | * | mp (°C) |
|---|---|---|---|---|---|
| 11 | H | 4-Cl | H | 3 | 146–147 |
| 12 | H | 3-CF$_3$ | H | 4 | 129–132 |
| 13 | H | 2-CH$_3$ | 3-Cl | 4 | 168–171 (d) |
| 14 | H | 2-CF$_3$ | H | 4 | 128–131 |
| 15 | H | 3-OCH$_3$ | H | 4 | 148–151 |
| 16 | H | 2-CH$_3$ | H | 4 | 217–219 |
| 17 | H | 3-CH$_3$ | H | 4 | HCl 198–201 |
| 18 | H | 2-F | H | 4 | 155–157 |
| 19 | 4-CH$_3$ | H | H | 4 | 150–156 (d) |
| 20 | 4-CH$_3$ | 3-Cl | H | 4 | 126–130 (d) |
| 21 | 4-CH$_3$ | 3-F | H | 4 | 135–136 |
| 22 | 4-CH$_3$ | 2-F | H | 4 | Ca.2H$_2$O 202–204 |
| 23 | 4-CH$_3$ | 3-CH$_3$ | H | 4 | 123–126 |
| 24 | 4-CH$_3$ | 3-Cl | 5-Cl | 4 | 198–201 |
| 25 | 4-CH$_3$ | 2-CH$_3$ | H | 4 | 147–149 |

Ex. No.: Example Number
*: The position of the benzene ring substituted by 4-thiazolin-2-ylideneamino group.
d: Decomposition
Ca: Calcium salt
H$_2$O: Hydrate
HCl: Hydrochloride

EXAMPLES 26–29

The following compounds are prepared by the similar procedures as described in Examples 9 and 10.

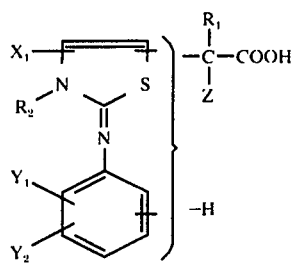

| Ex. No. | $Y_1$ | | mp (°C) |
|---|---|---|---|
| 26 | 2-F | Ca . 4H$_2$O | 175–178 |
| 27 | 4-Cl | Ca . 2H$_2$O | 163–166 |
| 28 | H | Ca . H$_2$O | 131–135 |
| 29 | 3-CH$_3$ | Ca . H$_2$O | 165–168 |

Ex. No.: Example Number
Ca: Calcium salt
H$_2$O: Hydrate

What is claimed is:

1. A member selected from the group consisting of a compound represented by the formula:

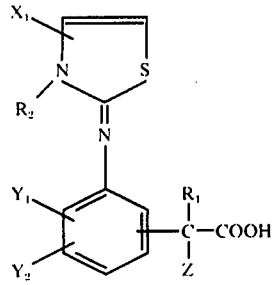

wherein $X_1$ represents hydrogen or methyl; $Y_1$ and $Y_2$ each represents hydrogen, halogen, $C_{1-3}$ alkyl, $C_{1-3}$ alkoxy or trifluoromethyl; $R_1$ represents hydrogen, methyl or ethyl; $R_2$ represents $C_{1-3}$ alkyl or $C_{3-5}$ alkenyl and Z represents hydrogen or carboxy and a pharmaceutically acceptable salt thereof.

2. A member selected from the group consisting of a compound represented by the formula:

wherein $X_1$ represents hydrogen or methyl; $Y_1$ and $Y_2$ each represents hydrogen, halogen, $C_{1-3}$ alkyl, $C_{1-3}$ alkoxy or trifluoromethyl; $R_1$ represents hydrogen, methyl or ethyl; $R_2$ represents $C_{1-3}$ alkyl or $C_{3-5}$ alkenyl and Z represents hydrogen or carboxy and a pharmaceutically acceptable salt thereof.

3. A compound of claim 2 wherein Z is hydrogen.

4. A compound of claim 2 wherein Z is hydrogen and $R_1$ is methyl.

5. A compound of claim 2 wherein both Z and $R_1$ are hydrogen.

6. A compound of claim 2 wherein Z is hydrogen and the group CHR$_1$COOH substitutes the para position of the benzene ring.

7. A compound of claim 2 wherein Z is hydrogen, $R_1$ is methyl and the group CHCH$_3$COOH substitutes the para position of the benzene ring.

8. A compound according to claim 2, namely 2-[2-chloro-4-(3-methyl-4-thiazolin-2-ylideneamino)-phenyl]propionic acid or a pharmaceutically acceptable salt thereof.

9. A compound according to claim 2, namely 2-[4-(3-methyl-4-thiazolin-2-ylideneamino)phenyl]propionic acid or a pharmaceutically acceptable salt thereof.

10. A compound according to claim 2, namely 2-[2-chloro-4-(3,4-dimethyl-4-thiazolin-2-ylideneamino)-phenyl]propionic acid or a pharmaceutically acceptable salt thereof.

11. A compound according to claim 2, namely 2[3-fluoro-4-(3-methyl-4-thiazolin-2-ylideneamino)-phenyl]propionic acid or a pharmaceutically acceptable salt thereof.

12. A compound according to claim 2, namely 2-[3-chloro-4-(3-methyl-4-thiazolin-2-ylideneamino)-phenyl]propionic acid or a pharmaceutically acceptable salt thereof.

13. A compound according to claim 2, namely 2-{3-chloro-4-[3-(2-propenyl)-4-thiazolin-2-ylideneamino]-phenyl}propionic acid or a pharmaceutically acceptable salt thereof.

14. A compound according to claim 2, namely 2-[3-chloro-4-(3,4-dimethyl-4-thiazolin-2-ylideneamino)-phenyl]propionic acid or a pharmaceutically acceptable salt thereof.

15. A compound according to claim 2, namely 2-[3,5-dichloro-4-(3-methyl-4-thiazolin-2-ylideneamino)phenyl]propionic acid or a pharmaceutically acceptable salt thereof.

16. A compound according to claim 2, namely 2-[3,5-dichloro-4-(3,4-dimethyl-4-thiazolin-2-ylideneamino)phenyl]-propionic acid or a pharmaceutically acceptable salt thereof.

17. A member selected from the group consisting of a compound represented by the formula:

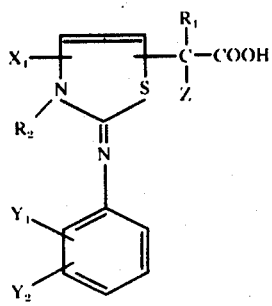

wherein $X_1$ represents hydrogen or methyl; $Y_1$ and $Y_2$ each represents hydrogen, halogen, $C_{1-3}$ alkyl, $C_{1-3}$ alkoxy or trifluoromethyl; $R_1$ represents hydrogen, methyl or ethyl; $R_2$ represents $C_{1-3}$ alkyl or $C_{3-5}$ alkenyl and Z represents hydrogen or carboxy and a pharmaceutically acceptable salt thereof.

18. A compound of claim 17 wherein Z is hydrogen.

19. A compound of claim 17 wherein Z is hydrogen and $R_1$ is methyl.

20. A compound of claim 17 wherein both Z and $R_1$ are hydrogen.

21. A compound according to claim 17, namely 2-[2-phenylimino-3-methyl-4-thiazolin-4-yl]propionic acid or a pharmaceutically acceptable salt thereof.

* * * * *